(12) United States Patent
Mak et al.

(10) Patent No.: US 11,278,205 B2
(45) Date of Patent: *Mar. 22, 2022

(54) MICROMETER SIZE MULTI-FUNCTIONAL PROBE FOR OCT AND ELECTRO-PHYSIOLOGICAL RECORDING

(71) Applicant: SYNAPTIVE MEDICAL INC., Toronto (CA)

(72) Inventors: Siu Wai Jacky Mak, Toronto (CA); Fangxin Li, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/106,407

(22) Filed: Nov. 30, 2020

(65) Prior Publication Data

US 2021/0076939 A1 Mar. 18, 2021

Related U.S. Application Data

(63) Continuation of application No. 16/434,475, filed on Jun. 7, 2019, now Pat. No. 10,952,617, which is a continuation of application No. 15/573,247, filed as application No. PCT/IB2016/056145 on Oct. 14, 2016, now Pat. No. 10,362,942.

(51) Int. Cl.
*A61B 5/00* (2006.01)
*A61B 5/06* (2006.01)
*A61B 5/291* (2021.01)
*A61B 3/00* (2006.01)
*A61B 3/10* (2006.01)

(52) U.S. Cl.
CPC .............. *A61B 5/0066* (2013.01); *A61B 3/00* (2013.01); *A61B 3/10* (2013.01); *A61B 5/0042* (2013.01); *A61B 5/0086* (2013.01); *A61B 5/065* (2013.01); *A61B 5/291* (2021.01)

(58) Field of Classification Search
None
See application file for complete search history.

(56) References Cited

U.S. PATENT DOCUMENTS

| | | | | |
|---|---|---|---|---|
| 10,952,617 | B2 * | 3/2021 | Mak | A61B 3/10 |
| 2005/0148836 | A1 * | 7/2005 | Kleen | A61B 5/0066 |
| | | | | 600/374 |
| 2013/0223702 | A1 * | 8/2013 | Holsing | A61B 8/0841 |
| | | | | 382/128 |

(Continued)

*Primary Examiner* — Shawn Decenzo

(57) ABSTRACT

A device and method for guided insertion of microelectrodes into tissue, the device involving a flexible optical fiber for optical coherence tomography imaging, a metal layer coating the optical fiber for recording electrical signals and an outer insulation layer coating the metal layer along the optical fiber length, and the method involving inserting an optical fiber coated with a metal layer and further coated with an insulation layer into a tissue, collecting intraoperative image data through the optical fiber by optical coherence tomography, receiving the image data on a computer and displaying the image on a monitor, using the image data to determine a location in the tissue, receiving an electrical nerve signal through the metal layer, and measuring the electrical nerve signal on an electro-physiological recording system.

20 Claims, 11 Drawing Sheets

(56) References Cited

U.S. PATENT DOCUMENTS

| | | | | |
|---|---|---|---|---|
| 2014/0121648 A1* | 5/2014 | Weiss | ............ | B29C 70/52 |
| | | | | 604/528 |
| 2016/0235480 A1* | 8/2016 | Scholl | ............ | A61B 17/86 |
| 2016/0287307 A1* | 10/2016 | Clark | ............ | A61B 5/4848 |
| 2017/0122928 A1* | 5/2017 | Naughton | ............ | G01N 33/4836 |
| 2017/0213013 A1* | 7/2017 | Piron | ............ | G16H 30/40 |
| 2017/0265947 A1* | 9/2017 | Dyer | ............ | G16H 40/63 |
| 2018/0271491 A1* | 9/2018 | Flanagan | ............ | A61B 5/0097 |
| 2018/0272042 A1* | 9/2018 | Borton | ............ | A61F 2/0077 |

* cited by examiner

MICROMETER SIZE MULTI-FUNCTIONAL PROBE FOR OCT AND ELECTRO-PHYSIOLOGICAL RECORDING

CROSS-REFERENCE TO RELATED APPLICATION(S)

This document is a continuation application claiming the benefit of, and priority to, U.S. patent application Ser. No. 16/434,475, filed on Jun. 7, 2019, entitled "MICROMETER SIZE MULTI-FUNCTIONAL PROBE FOR OCT AND ELECTRO-PHYSIOLOGICAL RECORDING," a continuation application claiming the benefit of, and priority to, U.S. patent application Ser. No. 15/573,247, filed on Nov. 10, 2017, entitled "MICROMETER SIZE MULTI-FUNCTIONAL PROBE FOR OCT AND ELECTRO-PHYSIOLOGICAL RECORDING," now U.S. Pat. No. 10,362,942, issued on Jul. 30, 2019, and a national phase entry application claiming the benefit of, and priority to, International Patent Application No. PCT/IB2016/056145, filed on Oct. 14, 2016, entitled "MICROMETER SIZE MULTI-FUNCTIONAL PROBE FOR OCT AND ELECTRO-PHYSIOLOGICAL RECORDING," all of which are incorporated herein by reference in their entirety.

FIELD

The present disclosure relates to a device for electro-physiological recording. More specifically, the present disclosure relates to a device for navigating electro-physiological recording.

BACKGROUND

Deep Brain Stimulation (DBS) is a surgical procedure used for the treatment of various diseases including Parkinson's disease and essential tremor. In the surgical procedure, a DBS lead is implanted at a target site to stimulate brain matter and thereby alleviate the clinical condition. To be effective and avoid deleterious side effects, the DBS lead must be located correctly within the brain matter. Therefore, before DBS lead placement is made, microelectrodes are typically used to penetrate deep brain matter and refine anatomical or imaging-based stereotactic targeting techniques. The microelectrode recording is used to precisely identify the target (i.e. thalamus, sub-thalamic nuclei (STN), GPi) in the brain for test stimulation before DBS lead placement is made. This recording involves a small metal wire, namely the microelectrodes recording leads (MER lead) that monitors the activity of nerve cells in the target area. Through the recording, the surgeon listens to the contrast in the electrical signal fired by the neurons and reads the waveforms on a computer to identify the stimulation target. The size of the MER lead is made extremely small to prevent bleeding and damage to the human brain as it is inserted deep into the human brain.

Currently, MER leads and stereotactic image guided systems, e.g., the Nexframe® stereotactic image guided system by Medtronics®, are the only tool the surgeon uses to locate the stimulation target. Intraoperative CT scans to augment information provided by preoperative MRI scans have been put forward to provide more accurate navigation of the MER. However, no intra-operative imaging device is currently available to provide real time images to the surgeon. In addition, the target for stimulation is typically very small, e.g., for STN 3 to 5 mm, which makes it difficult to locate if the brain shifts during surgery. If the initial path of the MER lead is offset such that the stimulation target is missed, the surgeon will typically pull back the lead and reinsert it a few millimeters away with no indication or guidance from any devices on what direction and distance to re-target the lead. This method is suboptimal and can cause significant damage to the brain. Reinserting the probe multiple times into a similar region of the brain causes increasing risk of excessive bleeding which causes brain damage as well as affecting stimulation effectiveness.

SUMMARY

The present disclosure addresses the foregoing challenges by way of a device and method for guided insertion of microelectrodes into tissue. In accordance with an aspect of the present disclosure, a probe for tissue recording in a medical procedure comprises a flexible optical fiber for optical coherence tomography imaging, having an optical fiber distal end and an optical fiber proximal end, a metal layer coating the optical fiber length for recording electrical signals, having a corresponding metal layer distal end and a corresponding metal layer proximal end; and an outer insulation layer coating the metal layer along the optical fiber length.

In accordance with another broad aspect of the present disclosure, a method for measuring electrical nerve signals in a tissue comprises inserting a probe having an optical fiber coated with a metal layer and further coated with an insulation layer into a tissue, collecting intraoperative image data through the optical fiber by optical coherence tomography, receiving the image data on a computer and displaying the image on a monitor, using the image data to determine a location in the tissue, receiving an electrical nerve signal through the metal layer and measuring the electrical nerve signal on an electro-physiological recording system.

A further understanding of the functional and advantageous aspects of the present disclosure can be realized by reference to the following detailed description and the appended drawings.

DETAILED DESCRIPTION

Figure 1:
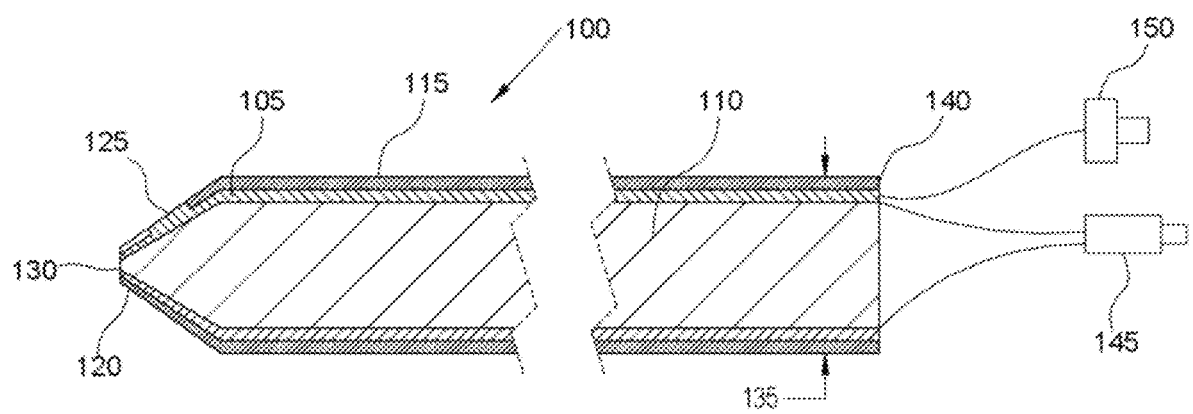
FIG. 1 illustrates a cross sectional view of a probe, in accordance with an embodiment of the present disclosure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

Understood is that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Several embodiments of the present disclosure seek to address the aforementioned inadequacies of existing devices and methods to support surgical procedures utilizing surgical tools.

The present disclosure involves an ultra-miniature probe that enables high resolution imaging for a DBS procedure using Optical Coherence Tomography (OCT) with a probe diameter similar to an MER lead (<350 microns). In addition, the probe can be used for simultaneous microelectode recording and stimulation.

Referring to FIG. 1, this diagram illustrates a probe 100 comprising a metal coated optical fiber in which the metal coating 105 is utilized for microelectrode recording and the optical fiber center 110 is utilized for OCT imaging, in accordance with an embodiment of the present disclosure. OCT is a noninvasive imaging technique, providing microscopic sectioning of biological tissues. The metal coating 105 allows electrical signals for microelectrode recording and tissue stimulation; and the metal coating 105 enables the fiber to be sterilizable. The metal coating 105 is further coated with insulation 115 along the length of the probe 100, but the insulation coating 115 is discontinuous near the probe distal end 120, thereby providing tissue contact 125 for electro-physiological recording. The optical fiber tip 130 at the probe distal end 120 is used for OCT imaging and is not coated with metal or insulation. The diameter 135 of the probe 100 is optimally less than 300 microns, although in alternate embodiments the probe may be less than 700 microns. On the proximal end 140 of the probe 100, the metal-coated optical fiber is split into an optical connector 145 for connection to an OCT system, and an electrical connector 150 for connection to an electro-physiological recording system. OCT images are generated as the probe penetrates through the brain by manual insertion. Furthermore, three-dimensional images may be formed if the probe is slowly spun around its longitudinal axis. For this purpose, a mechanical device may be attached to the probe to translate and rotate the probe to form two-dimensional and three-dimensional OCT images.

The probe 100 combines OCT (optical coherence tomography) imaging with an electrical probe, to integrate the electrical system with an optical imaging system and thereby provide an ultra-miniature probe for high resolution imaging, for example in deep brain stimulation. The optical imaging may be used to monitor insertion of the probe into brain matter, thereby providing a more informed insertion toward the target tissue. OCT contrast can be used to provide update registration of the probe position dynamically intraoperatively. OCT contrast may also provide micro-vasculature information, thereby reducing the risk of vessel damage and bleeding, and can assist in direction for lead reinsertion when the target is missed. The metal-coated optical fiber allows simultaneous microelectrode recording and tissue stimulation. OCT and polarization sensitive OCT (PS-OCT) can also provide contrast between white and grey matters in the brain enabling fiber tracts in the brain to be used as local landmarks to help targeting in addition to structural contrast in the brain tissue. For example, STN is surrounded by white matter which enables OCT to be used to help target the exact location of STN in addition to MER.

Figure 2:
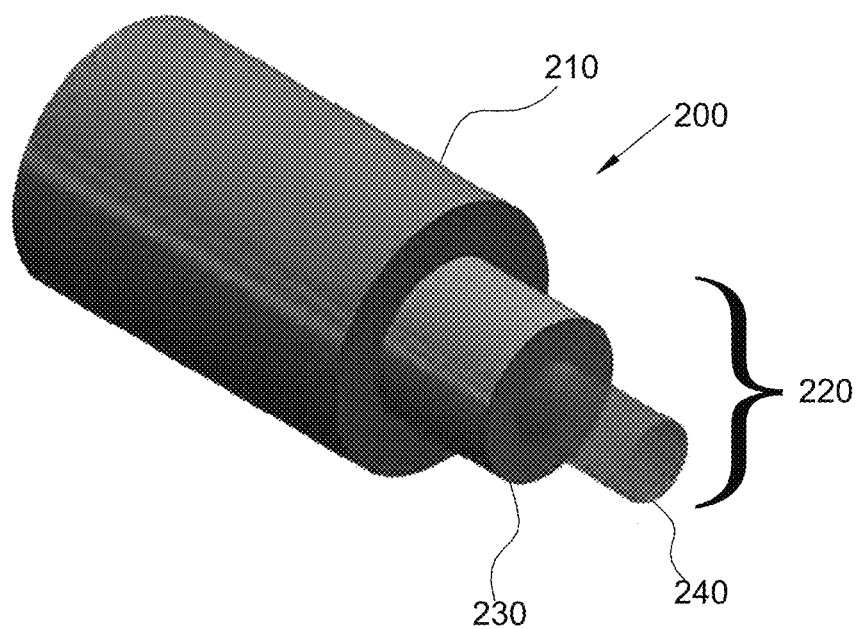
FIG. 2 illustrates a transverse view of a metal coated fiber structure, in accordance with an embodiment of the present disclosure.

Referring to FIG. 2, this diagram illustrates a metal coated fiber structure 200, with metal coating 210 surrounding the length of an optical fiber core 220, the optical fiber core 220 comprising a pure fused silica cladding and a germanium doped silica core, without insulation coating, in accordance with an embodiment of the present disclosure. On the distal end of the optical fiber 230, the fiber tip 240 is shaped in a way to focus infrared (IR) light for OCT imaging and an opening through the insulation layer (not shown) to the metal coating is created to allow tissue contact for electro-physiological recording.

Figure 3:
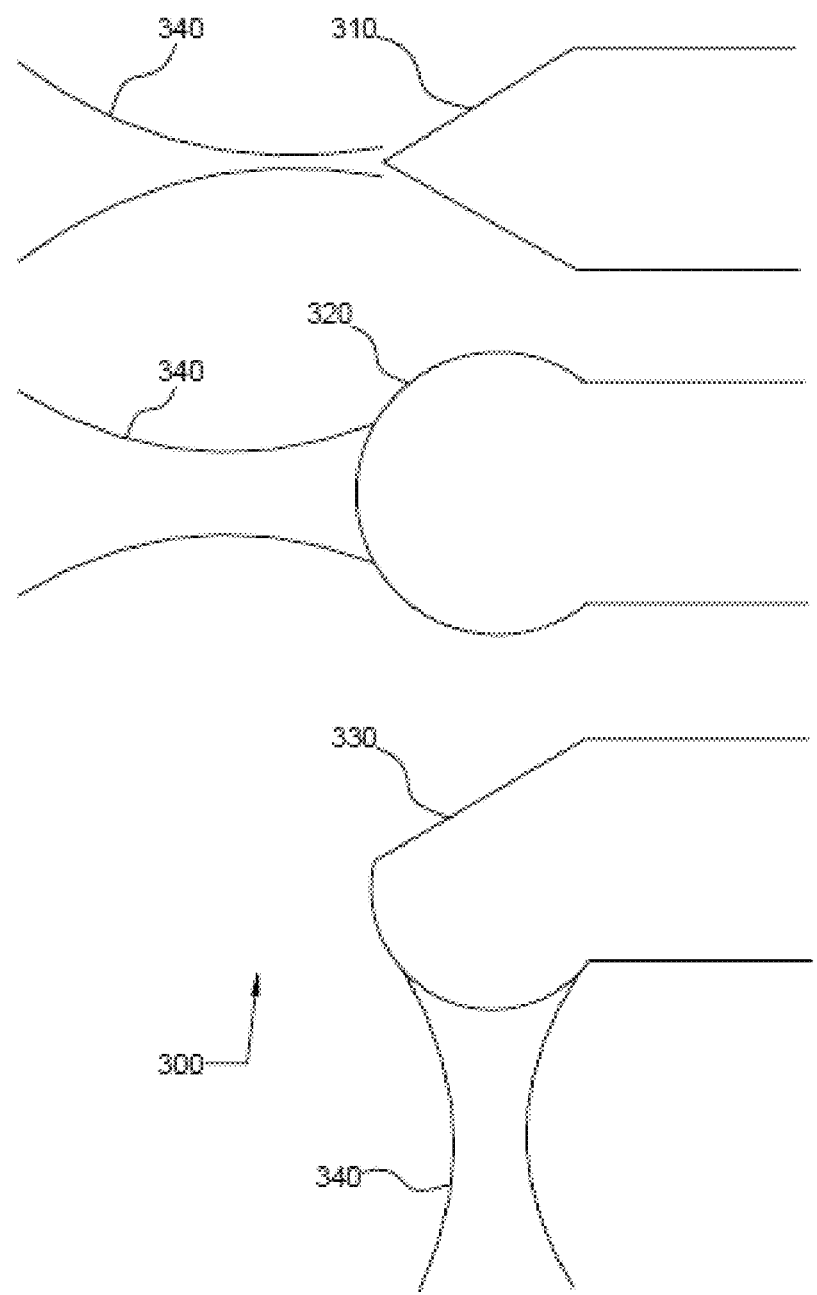
FIG. 3 illustrates an optical fiber tip, in accordance an embodiment of the present disclosure.

Referring to FIG. 3, this diagram illustrates an optical fiber tip 300 that can be shaped in multiple ways, in accordance with some embodiments of the present disclosure. For example, the fiber tip 300 can be shaped in a conical shape 310 to displace tissue radially during penetration with little axial tissue compression, thus reducing damage to the patient. The fiber tip 300 can also be shaped in a ball fashion 320, namely a ball lens, to enable larger light throughput 340 and maximize image sensitivity, or a semi-ball lens for side-firing light. The fiber tip 300 can also be shaped at a special angle 330 to reflect light 340 away from the forward configuration, e.g. side firing configuration.

Figure 4A:
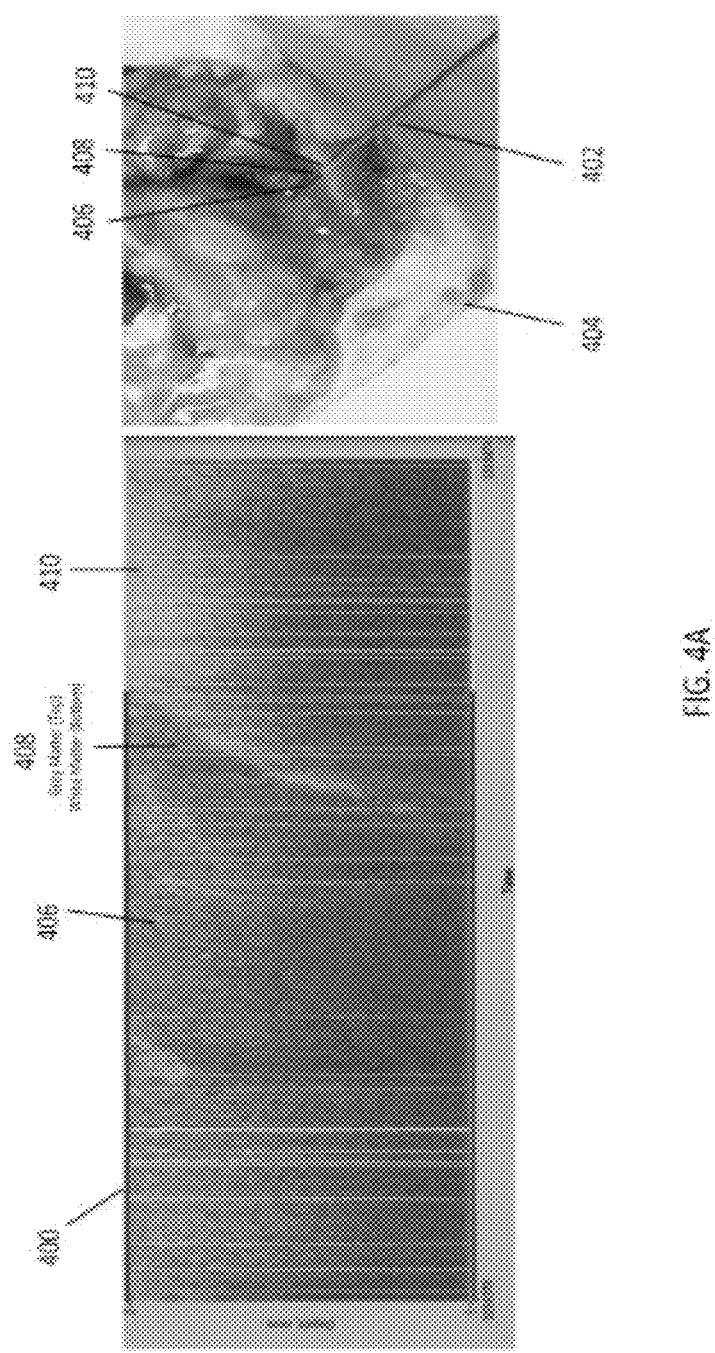
FIG. 4A illustrates an OCT image provided by an OCT probe penetrating a sheep brain, the OCT image having OCT contrast for landmarking and target identification, in accordance with an embodiment of the present disclosure.

Referring to FIG. 4A, this diagram illustrates an OCT image 400 provided by an OCT probe 402 penetrating a sheep brain 404, for example, in accordance with an embodiment of the present disclosure. Example images 400 are provided from optical coherence tomography (OCT) contrast in the sheep brain 404. The OCT images 400 are producible using an OCT probe 402, e.g., a GRINTech® Sidefire® probe, to acquire an image depth of 1 mm as the OCT probe 402 penetrates tissue of the sheep brain 404. The scatter, corresponding to grey matter 406, transition area 408, and white matter 410 in the sheep brain 404, is indicated above the OCT image 400.

Figure 4B:
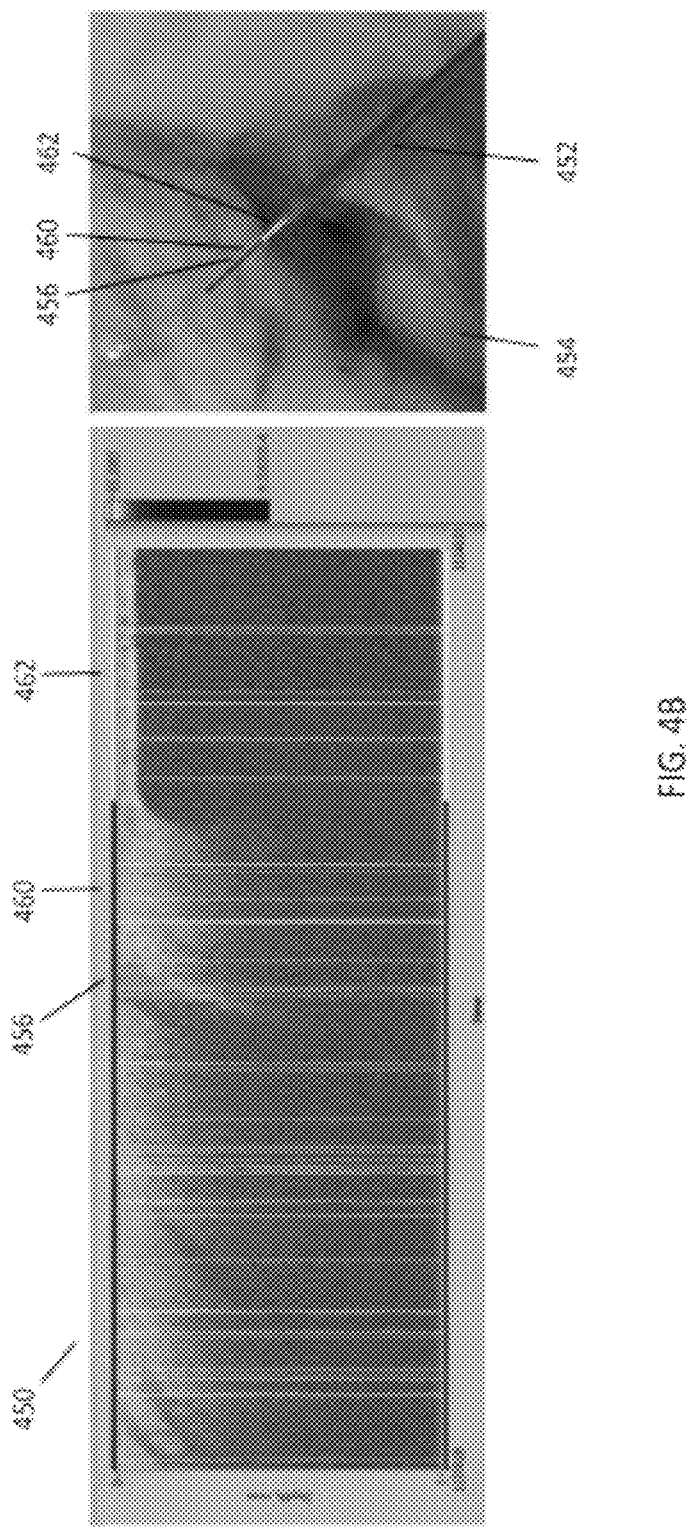
FIG. 4B illustrates an OCT image provided by an OCT probe penetrating a sheep brain, the OCT image having OCT contrast for landmarking and target identification, in accordance with an embodiment of the present disclosure.

Referring to FIG. 4B, this diagram illustrates an OCT image 450 provided by an OCT probe 452 penetrating a sheep brain 454, for example, in accordance with an embodiment of the present disclosure. In this example, scatter, as the OCT probe 452 passes through grey matter 456, white matter 460, and a cavity 462 in the sheep brain 454, is indicated above the OCT image 450.

For guiding placement of a probe through brain tissue, scattering contrast in optical coherence tomography (OCT) and polarization contrast in polarization-sensitive optical coherence tomography (PSOCT) can provide fiber tract contrast, which can be used as landmarks, enabling the surgeon to identify the region of the brain as the probe is penetrating into the brain (Jafri, M. S., et al., Journal of Biomedical Optics 10(5), 051603). For example, OCT images through the STN typically show abundant fine arterioles, whereas OCT images of the substantia nigra typically show thick ribbons of white matter. Thus, a lateral position of a probe track can be inferred from the length through the STN. If the thickness of the STN is about 1 mm, it is the lateral edge of the STN, whereas through the center of the STN the thickness of the STN is about 5 mm A trajectory that misses the STN and passes through only white matter fails to show the characteristic projection of the STN.

OCT imaging can provide the benefits in DBS, such as OCT contrast being used to dynamically intraoperatively update registration, OCT angiography intraoperatively providing micro-vasculature information as the probe penetrates, thereby assisting the surgeon in avoiding bleeding otherwise caused by cutting major arteries and veins, OCT providing very high imaging resolutions, e.g., in a range of greater than 1 micron, thereby enabling more accurate identification of the targets in millimeter scale, OCT non-destructively providing contrast into the tissue, thereby assisting in suggesting the reinsertion direction for the lead when the target is missed, and providing metal coated fibers that are sterilizable for use in surgery and in patients.

Figure 5A:
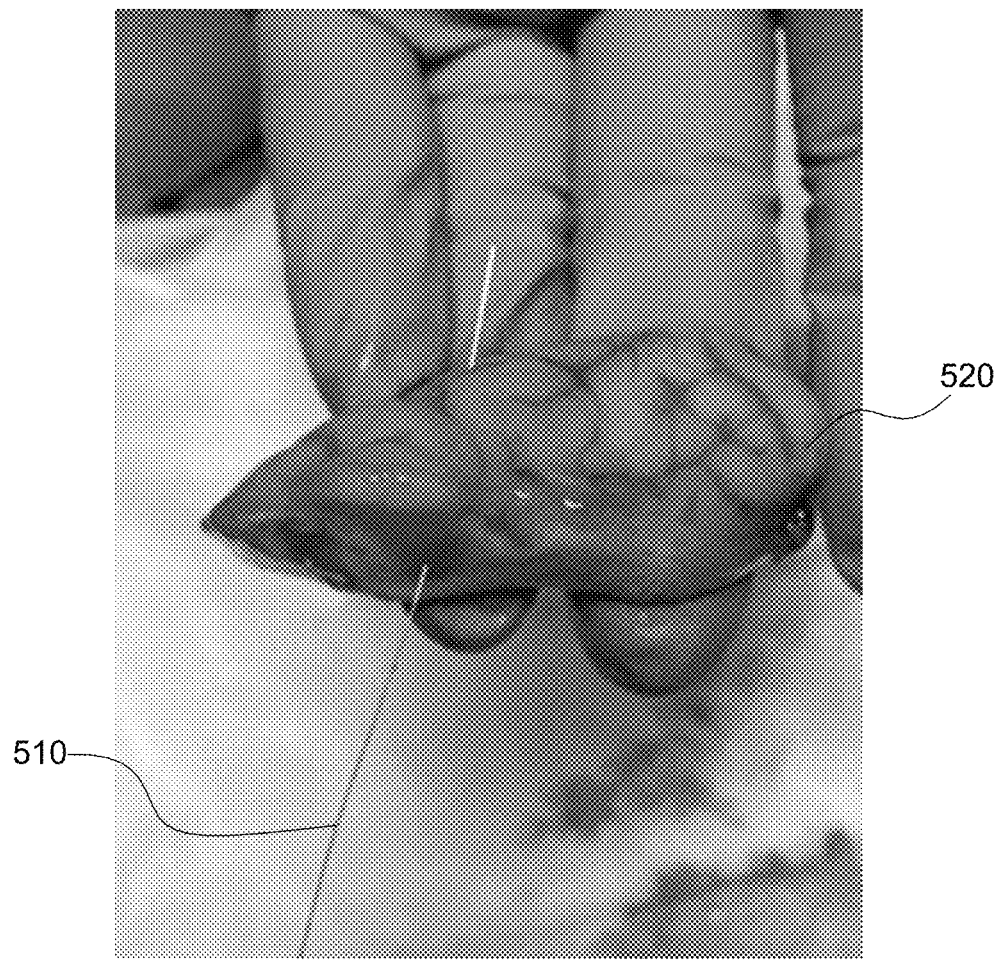
FIG. 5A illustrates a perspective view of a metal-coated fiber penetrated through a sheep brain, in accordance with an embodiment of the present disclosure.

Referring to FIG. 5A, this diagram illustrates, in a perspective view, metal coated fibers 510 that are very strong, thereby enabling the probe, e.g., the probe 402 or the probe 452, to penetrate into brain tissue, e.g., tissue of a sheep brain 520, with ease without damage to the fiber 510, in accordance with an embodiment of the present disclosure.

Figure 5B:
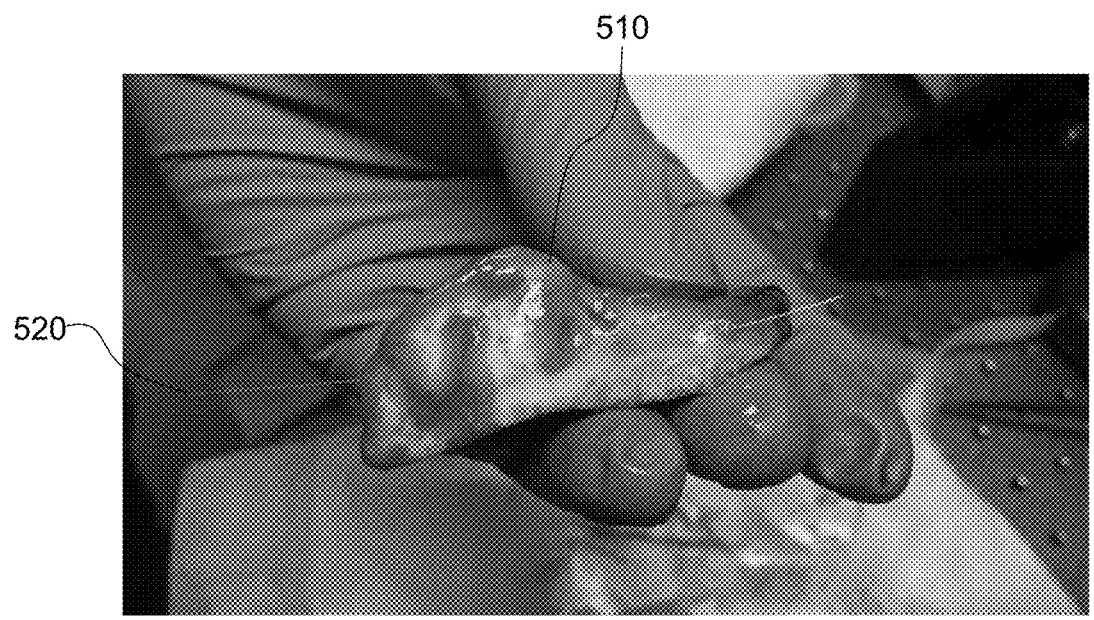
FIG. 5B illustrates another perspective view of a metal-coated fiber penetrated through a sheep brain, in accordance with an embodiment of the present disclosure.

Referring to FIG. 5B, this diagram illustrates, in another perspective view, metal coated fibers 510 that are very strong, thereby enabling the probe, e.g., the probe 402 or the probe 452, to penetrate into brain tissue, e.g., tissue of a sheep brain 520, with ease without damage to the fiber 510, in accordance with an embodiment of the present disclosure.

Figure 5C:
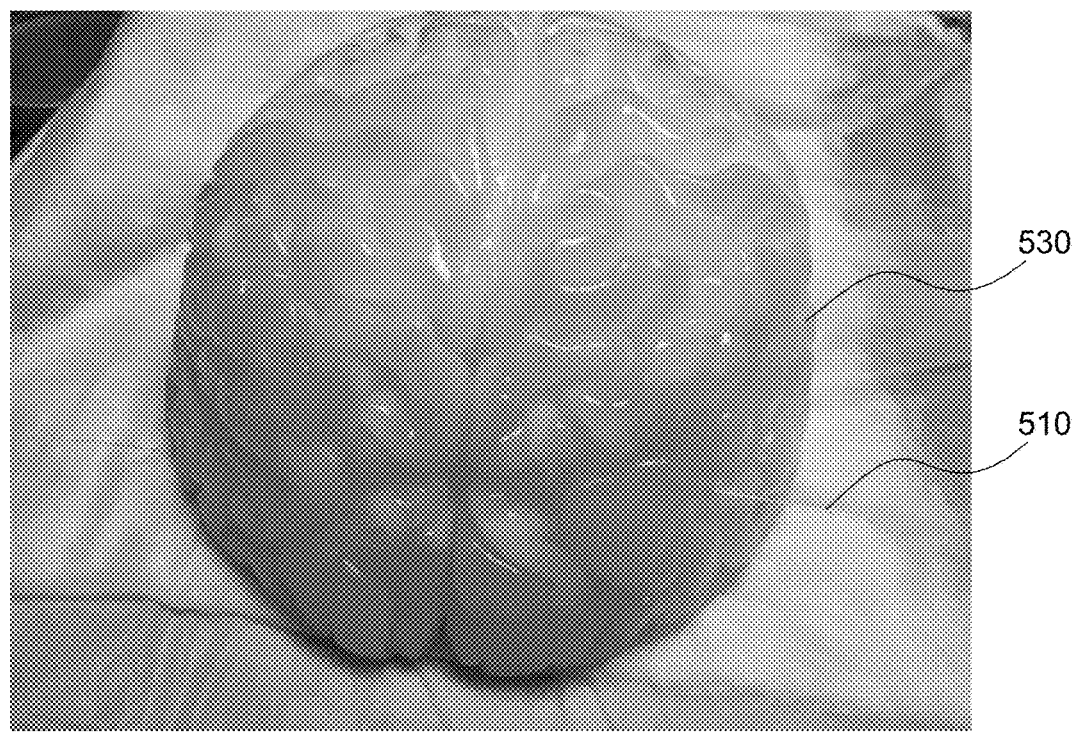
FIG. 5C illustrates a top view of a metal-coated fiber penetrated through a brain simulator, in accordance with an embodiment of the present disclosure.

Referring to FIG. 5C, this diagram illustrates, in a top perspective view, metal coated fibers 510 that are very strong, thereby enabling the probe, e.g., the probe 402 or the probe 452, to penetrate into brain tissue, such as tissue of a brain simulator 530, e.g., a BrightMatter® Simulator, with ease without damage to the fiber 510, in accordance with an embodiment of the present disclosure.

Figure 6:
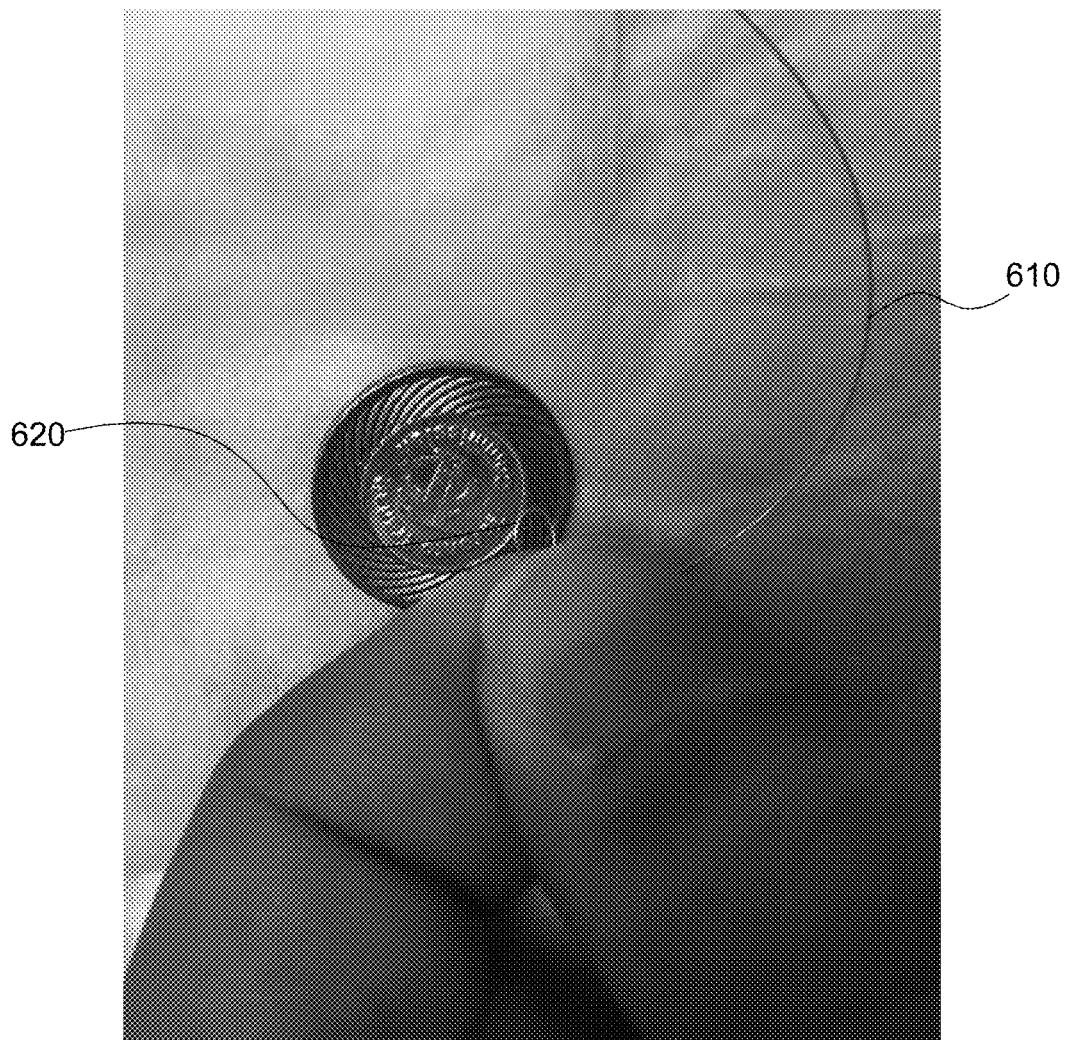
FIG. 6 illustrates a metal coated fiber bent, in accordance with an embodiment of the present disclosure.

Referring to FIG. 6, this diagram illustrates a metal coated fiber 620 that is highly flexible and easily bent to only 2 to 3 millimeters in diameter, in accordance with an embodiment of the present disclosure. When the metal coated fiber 620 breaks, the metal coated fiber 620 does not break into small pieces.

Figure 7A:
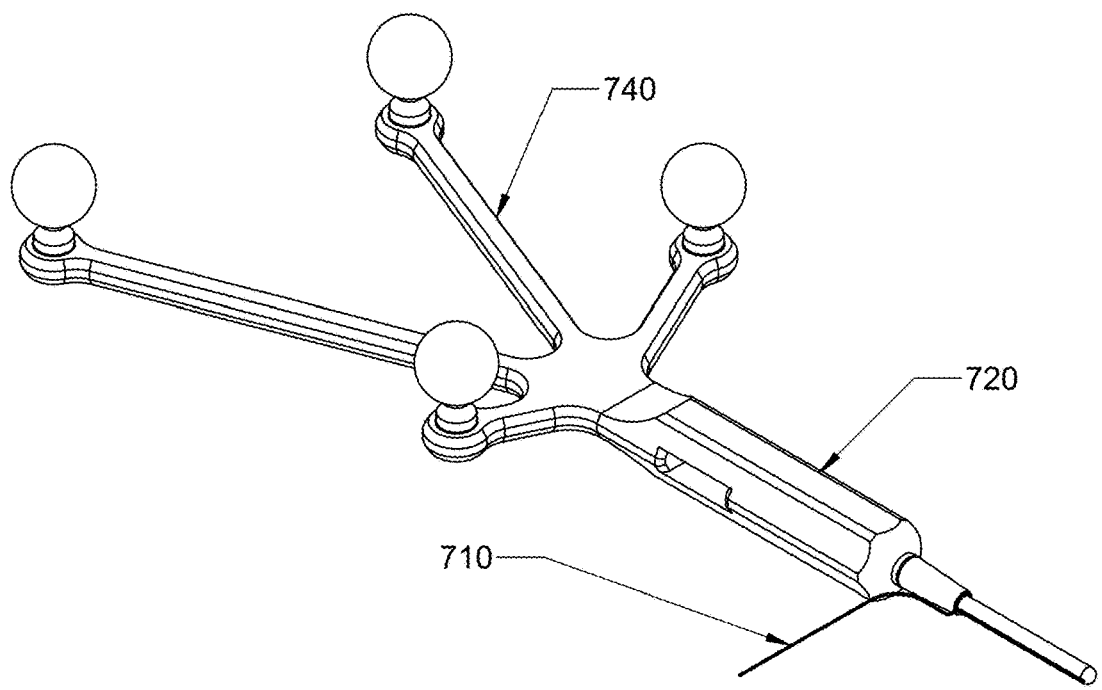
FIG. 7A illustrates a metal-coated optical fiber for use with the probe or the optical portion of the probe with a surgical pointer or a suction tool, wherein a probe is attached to a surgical pointer, in accordance with an embodiment of the present disclosure.

Referring to FIG. 7A, this diagram illustrates a metal-coated optical fiber 710 for use with the probe 710 or the optical portion of the probe with a surgical pointer 720 or a suction tool 730, in accordance with an embodiment of the present disclosure. In this way, as a target tissue is navigated with a pointer 720, the tissue may be imaged dynamically using the optical fiber for OCT contrast and electro-physiological recordings made of the surrounding tissue, thereby enhancing the ability to intraoperatively map the tissue.

Figure 7B:
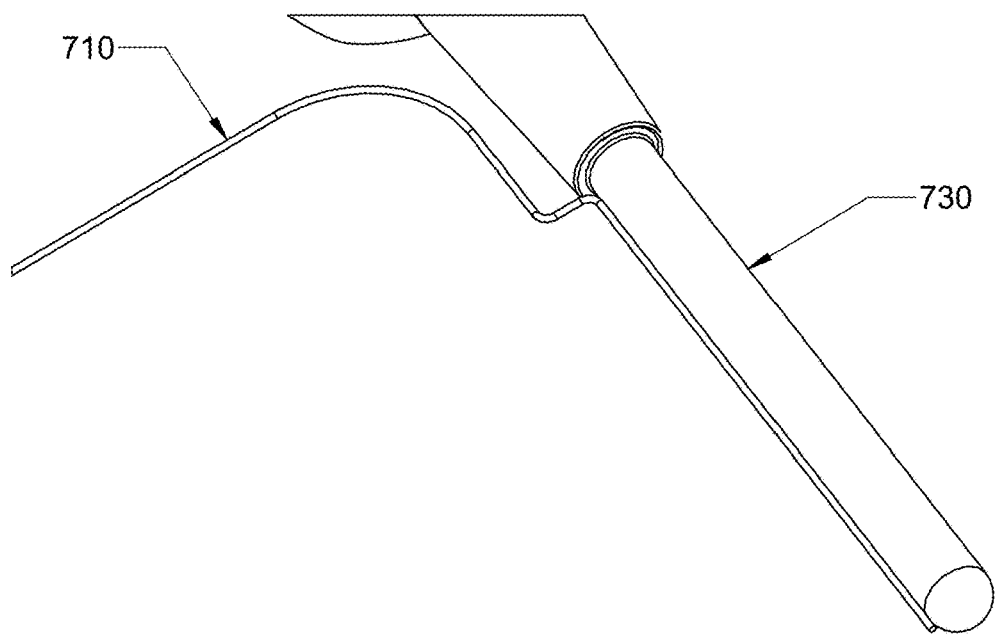
FIG. 7B illustrates a metal-coated optical fiber in use with the probe or the optical portion of the probe with a surgical pointer or a suction tool, wherein a probe is attached to a suction tool, in accordance with an embodiment of the present disclosure.

Referring to FIG. 7B, this diagram illustrates a metal-coated optical fiber 710 in use with the probe 710 or the optical portion of the probe with a surgical pointer 720 or a suction tool 730, in accordance with an embodiment of the present disclosure. The probe 710 could be used together with a surgical tool, e.g. suction tool 730 or a pointer tool 720, for optical and electro-physiological recordings to refine the mapping of the instrument within the brain tissue. Use of the probe 710 with either a pointer tool 720 or a suction device 730 may include a tracker tree 740 to allow for intraoperatively tracking the instruments.

Figure 8:
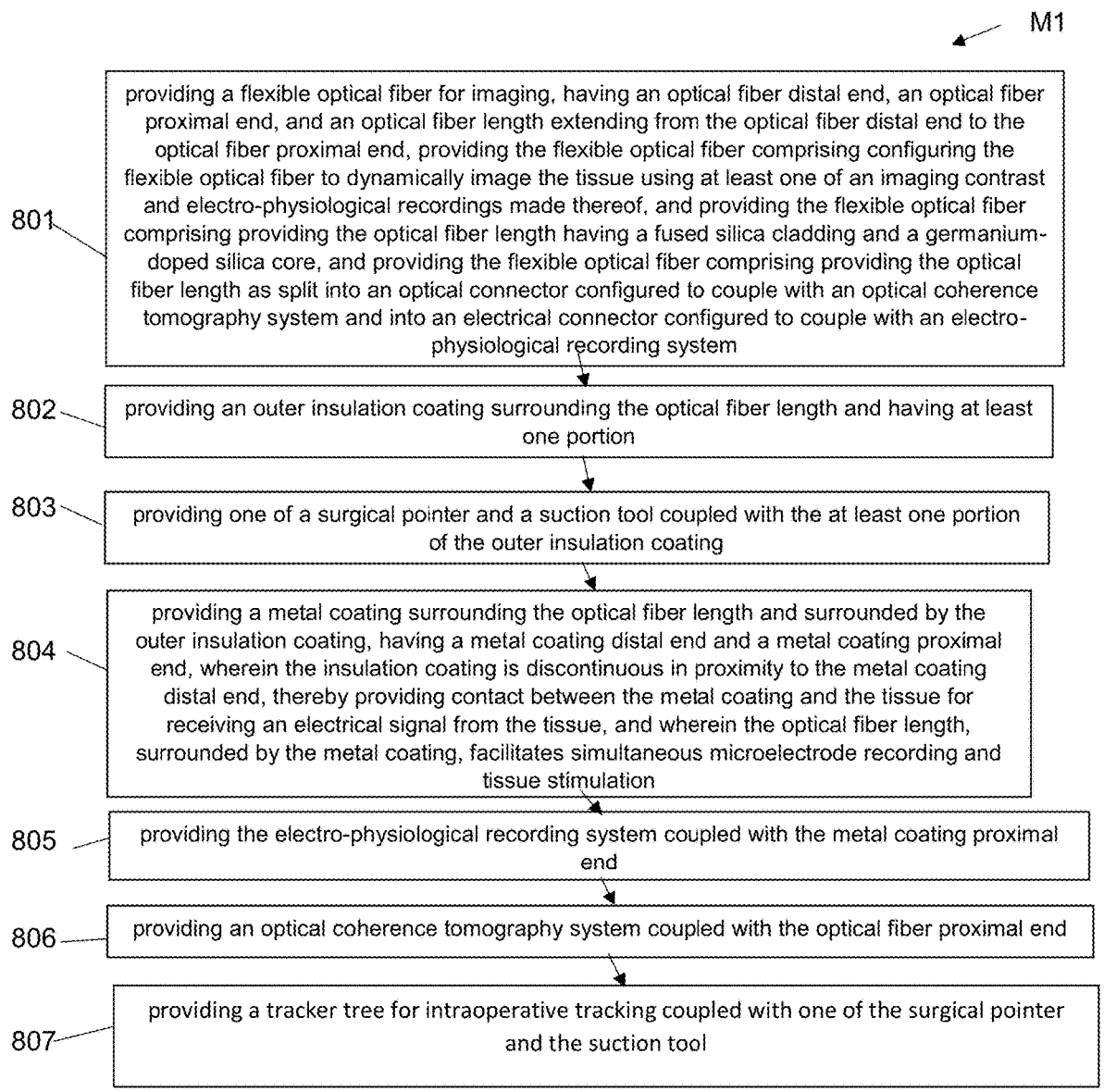
Referring to FIG. 8, this flow diagram illustrates a method of providing a surgical tool for recording an image of tissue during a medical procedure, in accordance with an embodiment of the present disclosure.

Referring to FIG. 8, this flow diagram illustrates a method M1 of providing a surgical tool for recording an image of tissue during a medical procedure, in accordance with an embodiment of the present disclosure. The method M1 comprises: providing a flexible optical fiber for imaging, having an optical fiber distal end, an optical fiber proximal end, and an optical fiber length extending from the optical fiber distal end to the optical fiber proximal end, as indicated by block 801; providing an outer insulation coating surrounding the optical fiber length and having at least one portion, as indicated by block 802; and providing one of a surgical pointer and a suction tool coupled with the at least one portion of the outer insulation coating, as indicated by block 803, providing the flexible optical fiber, as indicated by block 801, comprising configuring the flexible optical fiber to dynamically image the tissue using at least one of an imaging contrast and electro-physiological recordings made thereof, and providing the flexible optical fiber, as indicated by block 801, comprising providing the optical fiber length having a fused silica cladding and a germanium-doped silica core, and providing the flexible optical fiber, as indicated by block 801, comprising providing the optical fiber length as split into an optical connector configured to couple with an optical coherence tomography system and into an electrical connector configured to couple with an electro-physiological recording system.

Still referring to FIG. 8, the method M1 further comprises providing a metal coating surrounding the optical fiber length and surrounded by the outer insulation coating, having a metal coating distal end and a metal coating proximal end, wherein the insulation coating is discontinuous in proximity to the metal coating distal end, thereby providing contact between the metal coating and the tissue for receiving an electrical signal from the tissue, and wherein the optical fiber length, surrounded by the metal coating, facilitates simultaneous microelectrode recording and tissue stimulation, as indicated by block 804.

Still referring to FIG. 8, the method M1 further comprises at least one of: providing the electro-physiological recording system coupled with the metal coating proximal end, as indicated by block 805; providing an optical coherence tomography system coupled with the optical fiber proximal end, as indicated by block 806; and providing a tracker tree for intraoperative tracking coupled with one of the surgical pointer and the suction tool, as indicated by block 807. In the method M1, the medical procedure comprises deep brain stimulation, the optical fiber distal end comprises a shaped tip to focus light for facilitating using optical coherence tomography imaging, the shaped tip comprises one of: a conical shape, a spherical shape, and a semispherical shape, the optical fiber distal end comprises an angled distal end.

Figure 9:
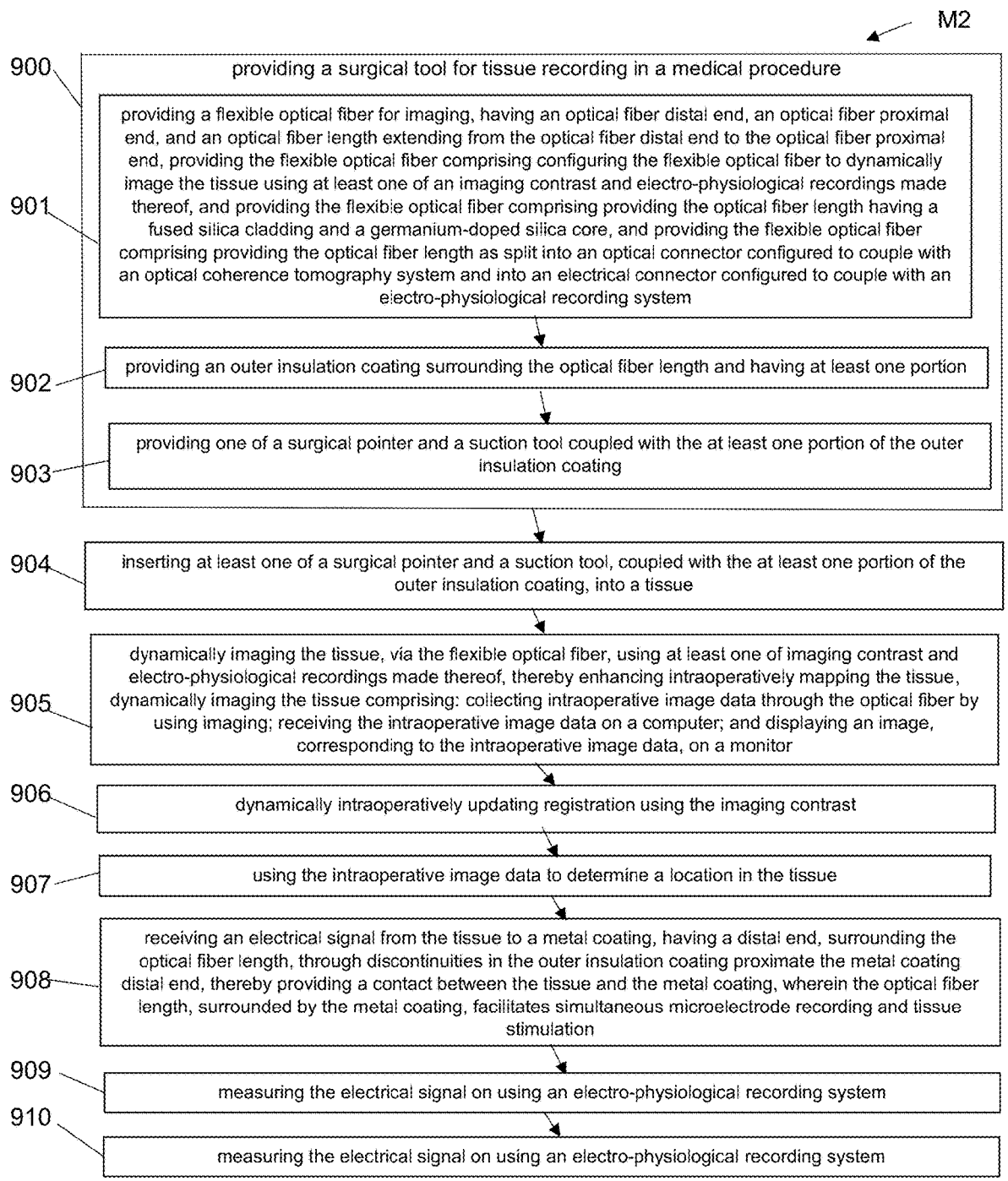
Referring to FIG. 9, this flow diagram illustrates a method of recording an image of tissue during a medical procedure, in accordance with an embodiment of the present disclosure.

Referring to FIG. 9, this flow diagram illustrates a method M2 of recording an image of tissue during a medical procedure, in accordance with an embodiment of the present disclosure. The method M2 comprises: providing a surgical tool for tissue recording in a medical procedure, as indicated by block 900, providing the surgical tool comprising: providing a flexible optical fiber for imaging, having an optical fiber distal end, an optical fiber proximal end, and an optical fiber length extending from the optical fiber distal end to the optical fiber proximal end, as indicated by block 901, providing the flexible optical fiber comprising providing the optical fiber length comprising providing a fused silica cladding and a germanium-doped silica core, and providing the flexible optical fiber comprising providing the optical fiber length as split into an optical connector configured to couple with an imaging system and into an electrical connector configured to couple with an electro-physiological recording system; providing an outer insulation coating surrounding the optical fiber length and having at least one portion, as indicated by block 902; and providing at least one of a surgical pointer and a suction tool coupled with the at least one portion of the outer insulation coating, as indicated by block 903; inserting at least one of a surgical pointer and a suction tool, coupled with the at least one portion of the outer insulation coating, into a tissue, as indicated by block 904; dynamically imaging the tissue, via the flexible optical fiber, using at least one of imaging contrast and electro-physiological recordings made thereof, thereby enhancing intraoperatively mapping the tissue, as indicated by block 905, dynamically imaging the tissue comprising: collecting intraoperative image data through the optical fiber by using imaging; receiving the intraoperative image data on a computer; and displaying an image, corresponding to the intraoperative image data, on a monitor; and dynamically intraoperatively updating registration using the imaging contrast, as indicated by block 906.

Still referring to FIG. 9, the method M2 further comprises: using the intraoperative image data to determine a location in the tissue, as indicated by block 907; receiving an electrical signal from the tissue to a metal coating, having a distal end, surrounding the optical fiber length, through discontinuities in the outer insulation coating proximate the metal coating distal end, thereby providing a contact between the tissue and the metal coating, wherein the optical fiber length, surrounded by the metal coating, facilitates simultaneous microelectrode recording and tissue stimulation, as indicated by block 908; measuring the electrical signal on using an electro-physiological recording system, as indicated by block 909; and stimulating the tissue using electrical signals from the metal coating to the tissue at the contact between the tissue and the metal coating, as indicated by block 910.

The specific embodiments described above have been provided by way of example; and understood is that these embodiments may be susceptible to various modifications and alternative forms. Further understood is that the claims are not intended to be limited to the particular forms disclosed, but, rather, the claims are understood to cover all modifications, equivalents, and alternatives falling within the spirit and scope of the present disclosure.

What is claimed:

1. A surgical tool for recording an image of tissue during a medical procedure, comprising:
   a flexible optical fiber for imaging, having an optical fiber distal end, an optical fiber proximal end, and
   an optical fiber length extending from the optical fiber distal end to the optical fiber proximal end;
   an outer insulation coating surrounding the optical fiber length and having at least one portion; and
   one of a surgical pointer and a suction tool coupled with the at least one portion of the outer insulation coating,
   the flexible optical fiber configured to dynamically image the tissue using at least one of imaging contrast and electro-physiological recordings made thereof, and
   the optical fiber length comprising a fused silica cladding and a germanium-doped silica core, and
   the optical fiber length is split into an optical connector configured to couple with an optical coherence tomography system and into an electrical connector configured to couple with an electro-physiological recording system,
   whereby intraoperatively mapping the tissue is enhanced, and
   whereby dynamically intraoperatively updating registration, using the imaging contrast is facilitated.

2. The tool as in claim 1, further comprising a metal coating surrounding the optical fiber length and surrounded by the outer insulation coating, having a metal coating distal end and a metal coating proximal end,
   wherein the insulation coating is discontinuous in proximity to the metal coating distal end, thereby providing contact between the metal coating and the tissue for receiving an electrical signal from the tissue, and wherein the optical fiber length, surrounded by the metal coating, facilitates simultaneous microelectrode recording and tissue stimulation.

3. The tool of claim 2, further comprising the electro-physiological recording system coupled with the metal coating proximal end.

4. The tool of claim 1, wherein the medical procedure comprises deep brain stimulation.

5. The tool of claim 1, wherein the optical fiber distal end comprises a shaped tip to focus light for facilitating using optical coherence tomography imaging.

6. The tool of claim 5, wherein the shaped tip comprises one of: a conical shape, a spherical shape, and a semispherical shape.

7. The tool of claim 1, wherein the optical fiber distal end comprises an angled distal end.

8. The tool of claim 1, further comprising an optical coherence tomography system coupled with the optical fiber proximal end.

9. The tool of claim 1, further comprising a tracker tree for intraoperative tracking coupled with one of the surgical pointer and the suction tool.

10. A method of providing a surgical tool for recording an image of tissue during a medical procedure, the method comprising:
providing a flexible optical fiber for imaging, having an optical fiber distal end, an optical fiber proximal end, and an optical fiber length extending from the optical fiber distal end to the optical fiber proximal end;
providing an outer insulation coating surrounding the optical fiber length and having at least one portion; and
providing one of a surgical pointer and a suction tool coupled with the at least one portion of the outer insulation coating,
providing the flexible optical fiber comprising configuring the flexible optical fiber to dynamically image the tissue using at least one of an imaging contrast and electro-physiological recordings made thereof, and
providing the flexible optical fiber comprising providing the optical fiber length having a fused silica cladding and a germanium-doped silica core, and providing the flexible optical fiber comprising providing the optical fiber length as split into an optical connector configured to couple with an optical coherence tomography system and into an electrical connector configured to couple with an electro-physiological recording system,
whereby intraoperatively mapping the tissue is enhanced, and
whereby dynamically intraoperatively updating registration, using the imaging contrast, is facilitated.

11. The method of claim 10, further comprising providing a metal coating surrounding the optical fiber length and surrounded by the outer insulation coating, having a metal coating distal end and a metal coating proximal end,
wherein the insulation coating is discontinuous in proximity to the metal coating distal end, thereby providing contact between the metal coating and the tissue for receiving an electrical signal from the tissue, and
wherein the optical fiber length, surrounded by the metal coating, facilitates simultaneous microelectrode recording and tissue stimulation.

12. The method of claim 11, further comprising providing the electro-physiological recording system coupled with the metal coating proximal end.

13. The method of claim 10, wherein the medical procedure comprises deep brain stimulation.

14. The method of claim 10, wherein the optical fiber distal end comprises a shaped tip to focus light for facilitating using optical coherence tomography imaging.

15. The method of claim 14, wherein the shaped tip comprises one of: a conical shape, a spherical shape, and a semispherical shape.

16. The method of claim 10, wherein the optical fiber distal end comprises an angled distal end.

17. The method of claim 10, further comprising providing an optical coherence tomography system coupled with the optical fiber proximal end.

18. The method of claim 10, further comprising providing a tracker tree for intraoperative tracking coupled with one of the surgical pointer and the suction tool.

19. A method of recording an image of tissue during a medical procedure, the method comprising:
providing a surgical tool for tissue recording in a medical procedure, providing the surgical tool comprising:
providing a flexible optical fiber for imaging, having an optical fiber distal end, an optical fiber proximal end, and an optical fiber length extending from the optical fiber distal end to the optical fiber proximal end, providing the optical fiber length comprising providing a fused silica cladding and a germanium-doped silica core, and providing the flexible optical fiber comprising providing the optical fiber length as split into an optical connector configured to couple with an imaging system and into an electrical connector configured to couple with an electro-physiological recording system;
providing an outer insulation coating surrounding the optical fiber length and having at least one portion; and
providing at least one of a surgical pointer and a suction tool coupled with the at least one portion of the outer insulation coating;
inserting at least one of a surgical pointer and a suction tool, coupled with the at least one portion of the outer insulation coating, into a tissue;
dynamically imaging the tissue, via the flexible optical fiber, using at least one of imaging contrast and electro-physiological recordings made thereof, thereby enhancing intraoperatively mapping the tissue, dynamically imaging the tissue comprising:
collecting intraoperative image data through the optical fiber by using imaging;
receiving the intraoperative image data on a computer; and
displaying an image, corresponding to the intraoperative image data, on a monitor; and
dynamically intraoperatively updating registration using the imaging contrast.

20. The method of claim 19, further comprising:
using the intraoperative image data to determine a location in the tissue;
receiving an electrical signal from the tissue to a metal coating, having a distal end, surrounding the optical fiber length, through discontinuities in the outer insulation coating proximate the metal coating distal end, thereby providing a contact between the tissue and the metal coating, wherein the optical fiber length, surrounded by the metal coating, facilitates simultaneous microelectrode recording and tissue stimulation;
measuring the electrical signal using an electro-physiological recording system; and stimulating the tissue using electrical signals from the metal coating to the tissue at the contact between the tissue and the metal coating.

\* \* \* \* \*